United States Patent [19]

Weinberger et al.

[11] Patent Number: Plant 7,355

[45] Date of Patent: Oct. 16, 1990

[54] PLUM CV. SUPLUMSEVENTEEN

[75] Inventors: John H. Weinberger; Timothy P. Sheehan, both of Fresno, Calif.

[73] Assignee: Superior Farming Company, Bakersfield, Calif.

[21] Appl. No.: 408,642

[22] Filed: Sep. 18, 1989

Related U.S. Application Data

[62] Division of Ser. No. 131,178, Dec. 10, 1987, abandoned.

[51] Int. Cl.[5] ..... A01H 5/00

[52] U.S. Cl. ..... Plt./38

[58] Field of Search ..... Plt./38

*Primary Examiner*—James R. Feyrer

*Attorney, Agent, or Firm*—William H. Elliott, Jr.

[57] ABSTRACT

A plum tree characterized by its very large, early ripening and fresh quality black fruit, oblate in shape with lenticels more prominent on the blossom end. Trees of the variety are of medium size and bear fruit regularly.

1 Drawing Sheet

This application is a division of our pending application Ser. No. 131,178, filed Dec. 10, 1987, now abandoned.

This invention relates to the discovery and asexual propagation of a new variety of hybrid plum tree, *Prunus salicina* cv. Suplumseventeen. The variety is an early seasoned plum bearing very large black plum fruit cultivated for fresh market use. It was discovered by John H. Weinberger and Timothy P. Sheehan near Fresno, Calif., and has as its seed parent Queen Rosa (unpatented). Its pollen parent is unknown.

The new variety cv. Suplumseventeen may be distinguished from other presently available commercial plum cultivars by the following combination of characteristics: its early ripening fresh quality black plum fruit of very large size; its round, slightly oblate fruit shape; its lenticels, more prominent on the fruit's blossom end; and its dark, purple-black exterior fruit skin color at full maturity.

As compared to the plum, El Dorado (unpatented), the fruit of the new variety is larger and smooth skinned, whereas the fruit of El Dorado is smaller and its skin is corrugated. Fruit of El Dorado ripens three weeks later than fruit of Suplumseventeen.

The new variety maintains these distinguishing characteristics through successive asexual propagations by, for example, budding.

The new variety may be distinguished from its seed parent, Queen Rosa, in the following combination of characteristics: Whereas the skin color of the fruit of the new variety is fully black in color, the skin color of the fruit of Queen Rosa is red. Fruit of Suplumseventeen ripens about two weeks earlier than does the fruit of Queen Rosa. The pollen parent of the new variety is not known.

The accompanying drawing illustrates, in full color, a typical stem and leaves of the new plum tree and the ripe fruit as viewed from the stem end and in profile. The drawing also illustrates the fruit sectioned in half from end to end, one-half of the fruit shown with the stone in place in the flesh and the other half shown with the stone removed from the flesh.

Throughout this specification, color names beginning with a small letter signify that the name of that color, as used in common speech, is aptly descriptive. Color names with capital letters designate values based upon the R.H.S. Colour Chart of The Royal Horticultural Society of London, England.

Plum trees of the new cultivated variety Suplumseventeen have been deposited before the filing date of this application in an orchard located at 5090 East Church Avenue, Fresno, Calif., and are identified there by applicant's identification number 401-72.

The descriptive matter which follows pertains to plum trees of the new variety grown in the environment of the San Joaquin Valley and is believed to apply to plants of the variety grown under similar conditions of soil and climate elsewhere.

TREE

The tree is of average size and average vigor. It is spreading in habit and vase-form in shape. The foliage tends towards medium density. The variety is half-hardy. The trees are productive, bearing their fruit regularly.

The trunk is of average thickness and the bark average in texture. The branches are average in caliper and are of medium smoothness. The branches have a dull surface appearance and carry an average number of medium-sized lenticels.

LEAVES

In general, leaves are of medium size, having an average length of about 9 cm. and an average width of about 4 cm. Leaves are elliptic in outline and flat in profile. Leaf blade tips curve downwardly at an acute angle. The finely serrate leaf margin has no undulation. The leaf apex is cuspidate to broadly acuminate; the leaf base is V-shaped. Leaves are of average thickness.

Leaf color on the upper surface is near Green 137A in color. The upper leaf surface is smooth in texture, of average glossiness, with no hairs present. The lower leaf surface is near Green 137C in color, weak in glossiness with no hairs present. The lower leaf surface is rugose in texture and has a dull surface appearance.

The petiole is of average length and average thickness. There are usually two medium-sized globose glands positioned on the petiole. Glands are brown in color. Stipules are presistent.

Leaf buds are of average size and conical in shape. Their position, relative to the shoot is adpressed. Leaf bud supports are of average medium size and are not decurrent.

Buds burst at a time average for the class.

Anthocyanin coloration in flowering shoots is absent. Shoots are of average thickness. Length between internodes is average for the class and buds are present in average density. Flowering shoots are distributed on spurs and one year old shoots. The ratio of wood (leaf) buds to flowering shoots is 1:2.

FLOWERS

Flower buds are small in size and of average length. Their shape is obtuse and positioning is free. Pubescence is absent. Flower bud color is brown.

Flowers attain full bloom, on the average, around the first week of March which is average as compared with similar varieties in the growing area of Fresno, Calif. Blooms last for a length of time average for the class. Flowers are small, about 2 cm. in diameter for a fully open flower, and a rosaceous in shape. Petals are overlapping. Color of the fully open flower is White 155D.

Peduncles are short in length, of average thickness, with no hairs.

The receptacle is of average depth. Pubescence of the inner and outer surfaces is absent.

Sepals are positioned adpressed to petals and are ovate in shape. Pubsecence of the inner and outer surfaces is absent. There are no flowers bearing double sepals present.

There are no flowers bearing double petals. Petals are of average size (around 0.7 cm.) and are circular in shape. Claws are medium in length and there is weak margin waviness present. Petal base angle is wide. The upper petal margin is entirely divided and pubescence of the inner and outer surfaces is absent. Color of the inner and outer petal surface is White 155D.

The position of the stigma is level as compared with anthers. Anther color just before dehiscence is yellow. Pollen color is yellow. Stamens are perigynous.

Pistils are almost always one in number.

Supplementary pistils are absent.

Pubescence is absent from the ovary. Pubescence at the base of the style is absent.

FRUIT

The fruit, as now described, was eating ripe. The size of the fruit of that stage of its development is uniformly large in size, having an axial diameter of about 5 cm. and a transverse diameter in the suture plane of about 6 cm. At right angles to the suture plane, the measurement is about 6 cm., thus indicating a practically uniform, symmetrical and globose shape slightly compressed transversely. The position of the maximum diameter is towards the middle. The fruit is symmetric about the suture line. Fruit ripens early in season and is for fresh market use. Keeping quality of the fruit is good as is the shipping quality.

The suture line extends from the base but is discontinuous at the apex and has slight depression beyond the pistil point. The ventral surface is rounded, with equal lips. There is not distinct depression of the apex. The pistil base does not persist. Pubescence at the apex is absent.

The stem cavity is rounded, and usually elongated in the plane of the suture, with the suture showing on one side. The depth of the stem cavity is about 1 cm., and its width about 1.5 cm. No markings are present. The base of the fruit is rounded and its apex is depressed in shape. The pistil point is apical in shape.

The glabrous stem is of average length, about 1 cm., and adheres with average strength to the stone.

The skin, which is of average thickness and of average texture is tenacious to the flesh and shows no tendency to crack during the dry season. Skin color is near Greyed-Purple 187A at full maturity. Down is wanting and a bloom is present. Skin possesses no roughness. Skin is slightly astringent to taste.

The color of the flesh is near Yellow 11C, and the surface of the pit cavity is near Yellow 16C. The amygdalin content is scant. Juice is rich and present in abundant amounts. The flesh has an average sugar content. Flesh texture is average to fine in firmness and meaty. Fibers are few, fine and tender. Fruit ripens evenly to produce fruit of good eating quality. The flavor is delicate and subacid and the aroma wanting. The ratio of stone to flesh is low.

The stone clings, adhering to flesh over its entire surface. Fibers of the stone are short and the stone parts from flesh smoothly. The stone is of average size, about 2 cm. in length and about 1.5 cm. in breadth. The width at the stalk end of the stone is about 0.2 cm. and about 0.8 cm. in thickness. The stalk end forms a right angle. The form of the stone in profile is generally elliptical and cuneate towards the base. Its form in ventral view is sub-globular. The stone's base is straight and its apex is acuminate. The hilum is oblong. The position of the stone's maximum breadth is toward the middle and the sides are generally equal. The surface of the stone is regularly ridged near the base. An outgrowing keel is partly developed. The ridges are jagged towards the base. The ventral stone edge is thin and without a wing throughout the dorsal stone edge is narrow with narrow grooves throughout. The color of the stone is near Orange 26B. The stone has a slight tendency to split during the dry season.

The fruit is well adapted for market use and to serve fresh. It has good shipping quality.

What is claimed is:

1. A new variety of plum tree cv. Suplumseventeen particularly distinguished and characterized by its early-ripening, fresh quality black plum fruit of very large size; is round, slightly oblate fruit shape; its lenticels more prominent on the fruit's blossom end and its dark purple-black exterior fruit skin color at full maturity, substantially as herein shown and described.

* * * * *

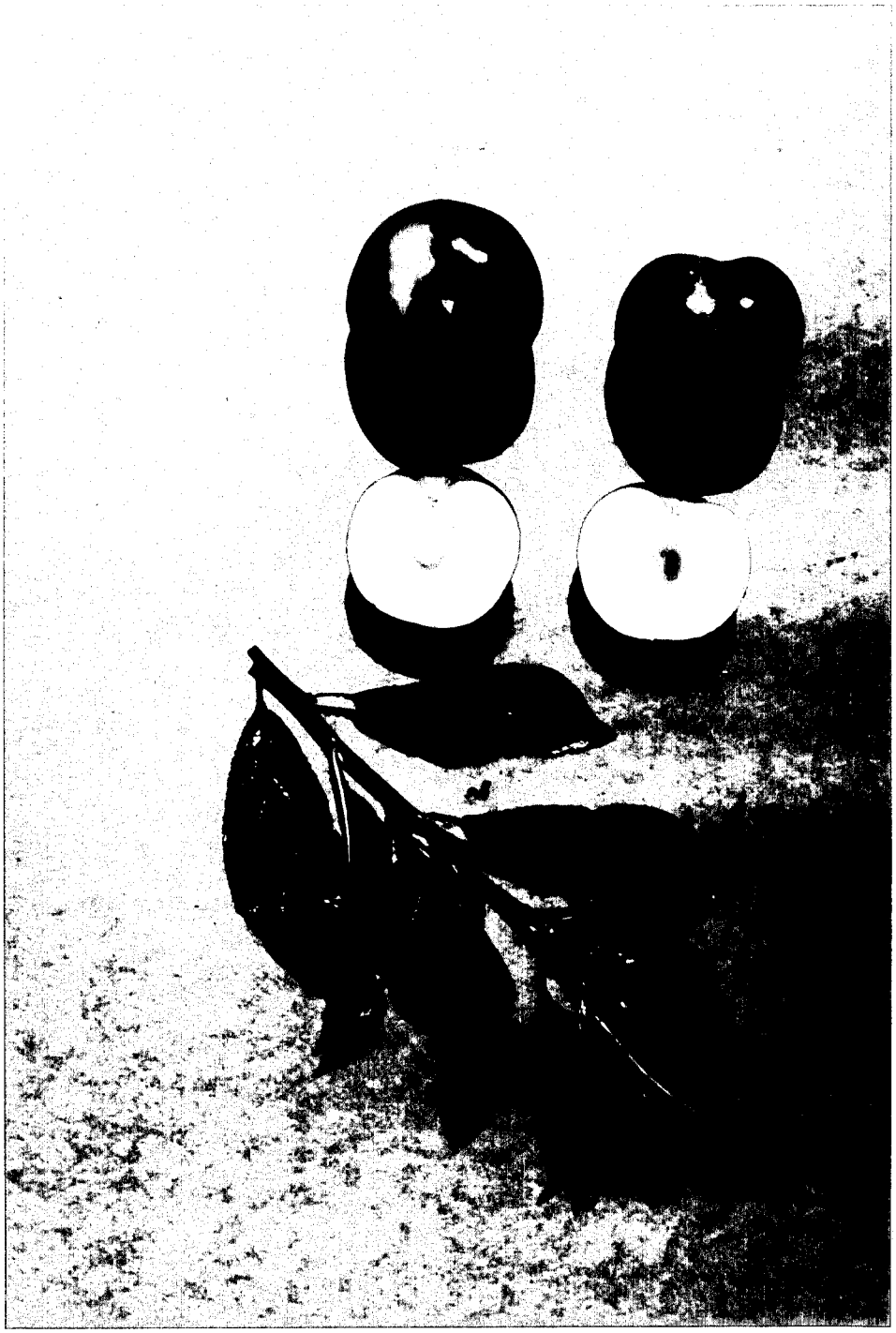

UNITED STATES PATENT AND TRADEMARK OFFICE

CERTIFICATE OF CORRECTION

PATENT NO. : Plant 7,355

DATED : Oct. 16, 1990

INVENTOR(S) : John H. Weinberger; Timothy P. Sheehan

It is certified that error appears in the above-identified patent and that said Letters Patent is hereby corrected as shown below:

ON TITLE PAGE: Item [73] the assignee should appear as follows:

Sun World, Inc.
Bakersfield, Calif.

Signed and Sealed this

Fourth Day of August, 1992

*Attest:*

*Attesting Officer*

DOUGLAS B. COMER

*Acting Commissioner of Patents and Trademarks*